United States Patent [19]

Gazzard

[11] Patent Number: 5,432,187
[45] Date of Patent: Jul. 11, 1995

[54] BENZIMIDAZOLE ANTHELMINTIC IN THE TREATMENT OF MICROSPORIDIAL INFECTIONS

[75] Inventor: Brian G. Gazzard, London, England

[73] Assignee: SmithKline Beecham, p.l.c., Brentford, United Kingdom

[21] Appl. No.: 117,160

[22] PCT Filed: Mar. 10, 1992

[86] PCT No.: PCT/GB92/00522

§ 371 Date: Sep. 15, 1993

§ 102(e) Date: Sep. 15, 1993

[87] PCT Pub. No.: WO92/16208

PCT Pub. Date: Jan. 10, 1992

[30] Foreign Application Priority Data

Mar. 25, 1991 [GB] United Kingdom ............... 9106278

[51] Int. Cl.$^6$ ........................................ A61R 31/415
[52] U.S. Cl. ............................... 514/388; 514/395
[58] Field of Search ............................. 514/395, 388

[56] References Cited

U.S. PATENT DOCUMENTS 3,915,986  10/1975  Gyurik et al. ................ 514/395

OTHER PUBLICATIONS

FR, M, 4761 (Chimetron) 20 Feb. 1967, see page 1, left $\propto$ hand column, lines 1–15.

Aids Care, vol. 3, No. 4, 19 Dec. 1991, E. K. Bagdades: "Current treatment of opportunistic infections in HIV disease", pp. 461–466.

STN Information services, file BIOSIS, abstract No. 91:446850, "Treatment of intestinal *microsporidiosis* with albendazole", VIII International Conference on Aids Science Challenging Aids; Florence, IT, Jun. 16–21, 1991, 464P, (vol. 1); 460P. (vol. 2).

J. Protozool, vol. 38, No. 6, 1991, Society of Protozoologists, 1991; E. U. Canning et al.: "In vitro and in vivo investigations of human microsporidia", pp. 631–635.

Primary Examiner—Jerome D. Goldberg
Attorney, Agent, or Firm—Janice E. Williams; Edward T. Lentz

[57] ABSTRACT

The present inventions relates to the use of certain benzimidazole compounds in the treatment of diseases caused by microsporidia organisms, in particular the treatment of diarrhea in patients infected with human immunodeficiency virus.

6 Claims, No Drawings

BENZIMIDAZOLE ANTHELMINTIC IN THE TREATMENT OF MICROSPORIDIAL INFECTIONS

This application is a 371 of PCT/GB92/00522 filed Mar. 23, 1992.

The present invention relates to the use of certain benzimidazole compounds in the treatment of diseases caused by microsporidia organisms, in particular the treatment of diarrhoea in patients infected with human immunodeficiency virus (HIV).

There are more than 500 species of the protozoa microsporidia which infect animals. Until the advent of acquired immune deficiency syndrome (AIDS) human infection was rare and confined to one or two cases of encephalitis and myositis. Now, however, microsporidium infection is common in the small intestine of HIV infected individuals and is thought to cause diarrhoea. In a recent study in the USA a third of patients in whom no other pathogen as a cause of diarrhoea had been uncovered, were found to have microsporidiosis infection in jejunal biopsy material (Human Pathology, 1990, 21(5), 475-81). Very similar figures were recently obtained in a UK study (Peacock et al., J. Clin. Path. 1991, in press). However, positive proof that Microsporidiosis is of pathogenic importance in the development of diarrhoea requires the ability to eradicate this organism with suitable chemotherapeutic agents or, alternatively, the development of suitable animal models. Such suitable chemotherapeutic agents have, until now, not been available.

The present invention fulfils this need and provides in a first aspect, the benzimidazole anthelmintic albendazole, for use in the manufacture of a medicament for use in the treatment of microsporidia infections, in particular in the treatment of microsporidia infection, for example diarrhoea-causing microsporidial infection, in patients infected with the human immunodeficiency virus (HIV).

In a broader aspect, the invention provides a benzimidazole anthelmintic for use in the manufacture of a medicament for use in the treatment of microsporidia infections, in particular in the treatment of microsporidia infection, for example diarrhoea-causing microsporidia infection, in patients infected with the human immunodeficiency virus (HIV).

The term 'benzimidazole anthelmintic' is intended to include any benzimidazole containing agent which is known to act as a broad spectrum anthelmintic. For example, in addition to albendazole, such compounds include fenbendazole, oxibendazole, mebendazole and parbendazole.

In a further aspect the present invention provides a method of treatment of microsporidial infection which comprises administration to a subject in need thereof of an effective amount of a benzimidazole anthelmintic, for example albendazole. In particular the invention provides a method for the treatment of microsporidial infection, for example diarrhoea-causing microsporidial infection, in patients infected with the human immunodeficiency virus (HIV).

When used in the present invention, the active agent is formulated in a standard pharmaceutical composition, for example in a tablet composition.

Suitable doses of active agent will be in the range of from 100 to 5000mg per day, the compound being administered in one or more discrete dosage units, once or twice a day, for as long as is necessary to treat the condition and maintain the patient free of infection. The size, frequency and duration of the dosage regimen will, of course, depend on the severity of the infection.

RESULTS

A study was carried out on 6 HIV infected individuals with diarrhoea and proven microsporidial infection on jejunal biopsy.

The patients were treated with albendazole (400 mg, b.i.d.) and within 1 week, 5 of the 6 had had dramatic symptomatic improvement with complete loss of diarrhoea and arrested weight loss. Subsequently, two patients died of non-diarrhoeal causes and of the remaining 4 who completed one month's treatment, two relapsed.

Jejunal biopsies performed following therapy in five of these patients have shown continuing evidence of Microsporidiosis but an apparent maturation arrest so that frequent meronts are seen but mature spores are not.

I claim:

1. A method of treatment of microsporidial infection which comprises orally administering to a subject in need thereof an effective amount of a benzimidazole anthelmintic selected from the group consisting of albendazole, fenbendazole, oxibendazole, mebendazole and parbendazole.

2. The method according to claim 1 in which the benzimidazole anthelmintic is albendazole.

3. The method according to claim 2 in which the subject is also infected with human immunodeficiency virus.

4. The method according to claim 3 in which the microsporidial infection is a diarrhoea-causing infection.

5. A method of treating diarrhoea caused by microsporidia organisms which comprises administering to a subject in need thereof an effective amount of a benzimidazole anthelmintic selected from the group consisting of albendazole, fenbendazole, oxibendazole, mebendazole and parbendazole.

6. The method according to claim 5 in which the benzimidazole anthelmintic is albendazole.

* * * * *